United States Patent [19]
Levin

[11] Patent Number: 5,827,281
[45] Date of Patent: Oct. 27, 1998

[54] INSULATED SURGICAL SCISSORS

[76] Inventor: John M. Levin, 412 Fairview Rd., Narbeth, Pa. 19072

[21] Appl. No.: 583,389

[22] Filed: Jan. 5, 1996

[51] Int. Cl.⁶ .................................................. A61B 17/39
[52] U.S. Cl. .............................. 606/51; 606/49; 606/50; 606/52; 606/170; 606/174
[58] Field of Search ............................... 606/45, 46, 48, 606/49, 50, 51, 52, 170, 174

[56] References Cited

U.S. PATENT DOCUMENTS

| | | |
|---|---|---|
| 1,813,902 | 7/1931 | Bovie . |
| 4,128,099 | 12/1978 | Bauer . |
| 4,375,218 | 3/1983 | DiGeronimo . |
| 4,499,899 | 2/1985 | Lyons, III . |
| 4,671,274 | 6/1987 | Sorochenko . |
| 4,890,610 | 1/1990 | Kirwan, Sr. . |
| 5,026,370 | 6/1991 | Lottick . |
| 5,116,332 | 5/1992 | Lottick . |
| 5,147,356 | 9/1992 | Bhatta . |
| 5,147,357 | 9/1992 | Rose et al. . |
| 5,171,256 | 12/1992 | Smith et al. . |
| 5,217,460 | 6/1993 | Knoepfler . |
| 5,234,453 | 8/1993 | Smith et al. . |
| 5,261,906 | 11/1993 | Pennino et al. ............... 606/46 |
| 5,295,990 | 3/1994 | Levin . |
| 5,308,311 | 5/1994 | Eggers et al. . |
| 5,330,471 | 7/1994 | Eggers . |
| 5,342,381 | 8/1994 | Tidemand . |
| 5,352,222 | 10/1994 | Rydell . |
| 5,356,408 | 10/1994 | Rydell ............................ 606/48 |
| 5,373,854 | 12/1994 | Kolozsi . |
| 5,396,900 | 3/1995 | Slater et al. . |
| 5,573,534 | 11/1996 | Stone ............................. 606/48 |

FOREIGN PATENT DOCUMENTS

| | | |
|---|---|---|
| 0593929A1 | 4/1994 | European Pat. Off. . |
| 107801 | 2/1978 | France . |

Primary Examiner—Lee S. Cohen
Attorney, Agent, or Firm—Caesar, Rivise, Bernstein, Cohen & Pokotilow, Ltd.

[57] ABSTRACT

An insulated surgical scissors, having a monopolar or a bipolar scissors construction, that can be used during laparoscopic, endoscopic and open surgery for cutting and coagulating tissue.

14 Claims, 7 Drawing Sheets

INSULATED SURGICAL SCISSORS

FIELD OF THE INVENTION

This invention relates generally to the field of insulated surgical scissors and more particularly to both monopolar and bipolar scissors constructions that can be specifically adapted for use in laparoscopic, endoscopic and open surgery surgical procedures.

BACKGROUND OF THE INVENTION

The insulation of a wide variety of insulated surgical coagulation devices other than scissors of the type forming the subject matter of this invention (e.g., biopsy devices and forceps) is known in the art. For example, note the surgical forceps disclosed in the following U.S. Pat. Nos. 5,217,460 (Knoepfler); 5,116,332 (Lottick); 5,026,370 (Lottick); 4,671,274 (Sorochenko); 4,890,610 (Kirwan, Sr. et al.); 5,147,357 (Rose et al.); 4,375,218 (DiGeronimo); 4,128,099 (Bauer); 1,813,902 (Bovie).

Also note the biopsy instruments disclosed in the following publications: U.S. Pat. No. 5,373,854 (Kolozsi); U.S. Pat. No. 5,295,990 (Levin); and European Patent Application 0 593 929 A1 (United States Surgical Corporation).

None of the above-identified publications relate to surgical scissors of the type forming the subject matter of the present invention.

A wide variety of surgical "cut and coagulation" scissors also are known in the art, as exemplified by U.S. Pat. Nos. 5,352,222 (Rydell); 5,342,381 (Tidemand); 5,234,453 (Smith et al.); 5,171,256 (Smith et al.); 5,147,356 (Bhatta); 4,499,899 (Lyons, III). Such surgical scissors are utilized for purposes that are significantly different from the previously identified coagulating biopsy or forceps devices.

The apparatus disclosed by Rydell is a surgical scissors with a bipolar coagulation feature. The scissors disclosed therein comprises a pair of opposed blade members pivotally joined to one another through an insulated bushing member. Each of the blade members comprises a blade support and a blade, each fabricated from a metal but yet separated by a dielectric bonding agent. Cutting is performed at the blade level and cauterization occurs through the passage of electricity from one blade support and through the tissue to the other blade support. In other words, the passage of electricity is not through either of the blades that cut the tissue. Instead, electricity flows from one blade support (above and below the cut made by the blades), through the tissue trapped between the blade members, and into the other blade support.

The apparatus disclosed by Tidemand is a combination bipolar scissors and forceps instrument. The scissors disclosed therein comprises a pair of interfacing blade surfaces. Each of the interfacing blade surfaces comprises an insulative ceramic layer of approximately 0.020 inches. During scissoring action, a gap of approximately 0.040 inches is created between the interfacing scissors surfaces. Tidemand states that this gap is small enough to allow an RF current applied to the interfacing blade members to "bridge" the gap and effect a cauterization on any tissue trapped between the blades.

The apparatus disclosed by Smith et al. ('453) is a disposable laparoscopic scissors utilizing cobalt-based alloy scissor elements that can be double acting (two movable jaws) or single acting (a single movable jaw in combination with a fixed jaw) and includes a plastic shrink wrap applied to the aluminum tube.

The apparatus disclosed by Smith et al. ('256) is also a disposable laparoscopic scissors that can be double acting or single acting and includes plastic shrink wrap applied to the aluminum tube and portions of the actuation means at the working end of the instrument to electrically insulate the instrument.

The apparatus disclosed by Bhatta is a scissors-like surgical instrument with a cutting and cauterizing heat source such as a hot wire element or a laser transmission fiber carried in at least one of the jaw members.

The apparatus disclosed by Lyons, III is a rotary cutting scissors for microsurgery that includes an internal fiber light source for illuminating the surgical area.

Even in view of the above-described prior art disclosures, it is the applicant's belief that a need still exists for an improved surgical scissors construction that allows the surgeon to cut tissue and to immediately coagulate the opening created by the cut while at the same time minimizing or eliminating any burning of surrounding tissue. In addition, it is important to be able to restrict the electric current flow through the patient's tissue when using such an apparatus.

OBJECTS OF THE INVENTION

Accordingly, it is a general object of this invention to provide a surgical scissors and a method of use which addresses the aforementioned needs.

It is a further object of this invention to provide a surgical scissors that can cut and coagulate tissue while minimizing or eliminating any burning of surrounding tissue.

It is yet another object of this invention to provide a surgical scissors that can cut and coagulate tissue while minimizing the generation of any smoke that may obstruct the surgeon's view of the surgical area.

It is still yet a further object of this invention to provide a surgical scissors that can cut and coagulate tissue while localizing the passage of electric current through surrounding tissue.

It is still yet another object of this invention to provide a laparoscopic surgical scissors that can cut and coagulate tissue while minimizing any burning of surrounding tissue.

It is even yet a further object of this invention to provide a laparoscopic surgical scissors that can cut and coagulate tissue while minimizing the generation of any smoke that may obstruct the surgeon's view of the surgical area.

SUMMARY OF THE INVENTION

These and other objects of the instant invention are achieved by providing a surgical scissors for cutting and coagulating tissue during surgery while minimizing electrical and thermal contact of the scissors with surrounding tissue. The scissors comprises a pair of opposing cutting blades pivotally connected to allow for shearing action of any tissue confined between the cutting edge of the cutting blades. The blades have confronting surfaces. In addition, the pair of opposing cutting blades are entirely covered with an electrically and thermally insulative material, except along corresponding segments of the confronting surfaces. Furthermore, a power source is coupled to at least one of the pair of opposing cutting blades for electrically and thermally energizing at least one of the pair of blades (e.g., forming a monopolar insulated surgical scissors). Finally, the insulated surgical scissors includes a closed condition wherein the confronting surfaces form overlapping surfaces and wherein the overlapping surfaces include the corresponding segments.

In a second embodiment of this invention the monopolar insulated surgical scissors comprises a pair of opposing cutting blades having respective flattened tips and where the cutting blades are entirely covered with an electrically and thermally insulative material, except along facing surfaces of the flattened tips.

In a third embodiment of this invention the scissors comprises a pair of opposing cutting blades pivotally connected to allow for shearing action of any tissue confined between the cutting edge of the cutting blades. In addition, the pair of opposing cutting blades are entirely covered with an electrically and thermally insulative material, except along a segment of the cutting edge of each of the cutting blades. Furthermore, the pair of opposing cutting blades are constructed so that the cutting edges make contact with each other simultaneously whenever there is no tissue disposed therebetween. The high side of a power source is coupled to one of the pair of opposing cutting blades while the low side of the power source is coupled to the other of the pair of opposing cutting blades for electrically and thermally energizing the pair of blades while restricting the flow of electrical current to the surgical scissors only to form a bipolar insulated surgical scissors.

In a fourth embodiment of this invention, the bipolar insulated medical scissors comprises a pair of opposing cutting blades having respective flattened tips and where the cutting blades are entirely covered with an electrically and thermally insulative material, except along facing surfaces of the flattened tips.

In a fifth embodiment of this invention, the scissors comprises a pair of opposing cutting blades pivotally connected to allow for cutting of any tissue confined between the cutting edges of the cutting blades much like a nail clipper. In addition, the pair of opposing cutting blades are entirely covered with an electrically and thermally insulative material, except along facing surfaces of the flattened tips. Furthermore, the pair of opposing cutting blades are constructed so that the cutting edges make contact with each other simultaneously whenever there is no tissue disposed therebetween. The high side of a power source is coupled to one of the pair of opposing cutting blades while the low side of the power source is coupled to the other of the pair of opposing cutting blades for electrically and thermally energizing the pair of blades while restricting the flow of electrical current to the surgical scissors only to form another bipolar insulated surgical scissors.

In a sixth embodiment of this invention, each of the previously described embodiments are employed with hand grips to permit each of these embodiments to be used during open surgery.

DESCRIPTION OF THE DRAWINGS

Other objects and many of the attendant advantages of this invention will be readily appreciated as the same becomes better understood by reference to the following detailed description when considered in connection with the accompanying drawings wherein.

DESCRIPTION OF THE PREFERRED EMBODIMENTS OF THE INVENTION

Figure 1:
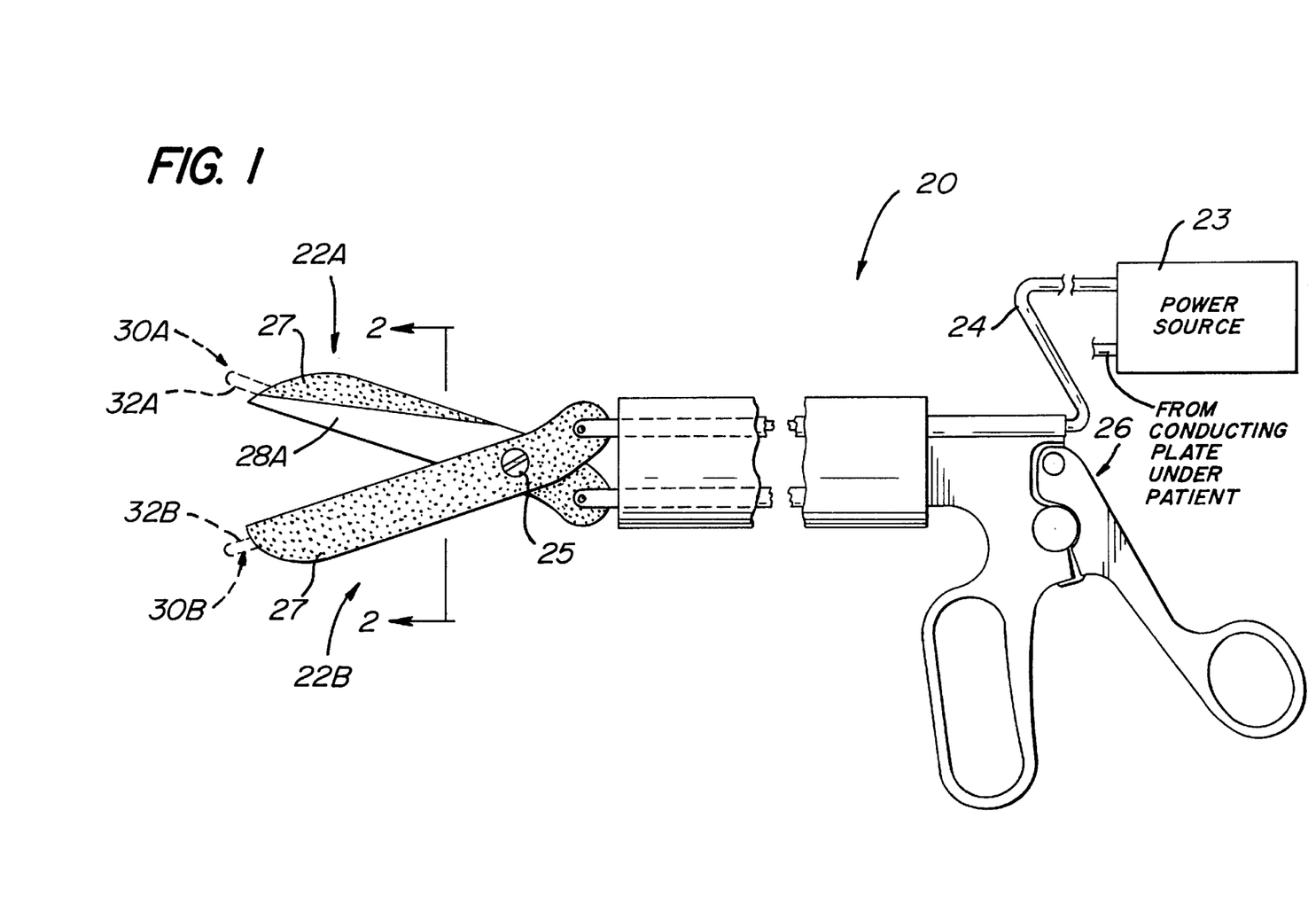
FIG. 1 is an enlarged fragmentary side elevational view of one preferred monopolar embodiment of an insulated surgical scissors in accordance with this invention.

Referring now in greater detail to the various figures of the drawing wherein like reference characters refer to like parts, an insulated surgical scissors constructed in accordance with the present invention is shown generally at 20 in FIG. 1. The insulated surgical scissors 20 cuts tissue by severing tissue wedged between a pair of scissors jaws 22A and 22B as the jaws overlap, much like any other type of surgical scissors. In one preferred embodiment, the insulated surgical scissors 20 forms the working end of a laparoscopic tool, thereby permitting the insulated surgical scissors 20 to be used during laparoscopic surgery. The manner in which the jaws 22A and 22B are operated by the surgeon through actuation of a handle portion of the laparoscopic tool can be similar to that set forth in U.S. Pat. No. 5,234,453 (Smith et al.), the disclosure of which is incorporated by reference herein, and does not constitute a limitation on the present invention. Therefore, a detailed explanation of this latter operation is omitted from this application. It should be understood that mechanisms for controlling or effecting relative movement of jaws at the distal end of a surgical device (both laparoscopic and non-laparoscopic) and their actuation by handles at the proximal end are well-known in the art and for purposes of brevity will not be further discussed herein.

In addition, the insulated surgical scissors 20 of the invention is electrically energized for accomplishing the coagulation of blood vessels that are severed during the cutting operation. In particular, an electrical conductor 24 provides electrical energy from a conventional power source 23 to the scissors 20. The scissors 20 comprises a monopolar configuration, i.e., electrical energy is delivered from the power source 23 via a single conductor to the scissors jaws 22A and 22B (each comprising a metal such as stainless steel for conducting electricity), with both jaws 22A and 22B being at the same voltage. The return for the electrical energy from the scissors 20 is through the patient (not shown) to a large surface (e.g., a conducting plate, not shown) located underneath the patient and then back to the power source 23, as is well-known in the art. As can be seen in FIG. 1, the electrical conductor 24 enters the laparoscopic tool at the proximal end 26 of the tool and is fed through the tool where the conductor 24 passes the electrical energy to the lower jaw 22B and to the upper jaw 22A via the conductive pivot fastener 25.

Figure 2:
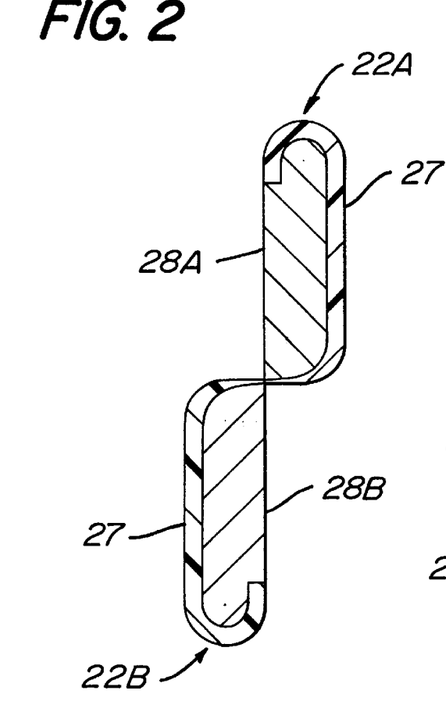
FIG. 2 is an enlarged view of the insulated scissors of FIG. 1 taken along line 2—2.
Figure 2A:
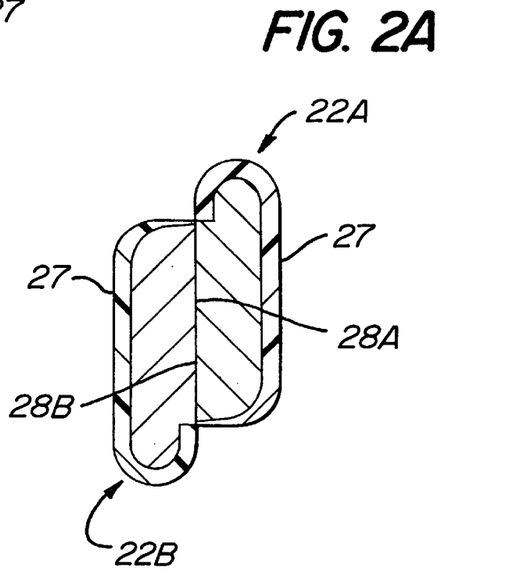
FIG. 2A is an enlarged view of the insulated scissors of FIG. 1 taken along line 2—2 but with the scissors in a closed condition.

Referring to FIGS. 2 and 2A, it should be noted that the insulated surgical scissors 20 is completely insulated (e.g., using a ceramic material), both electrically and thermally, on all of its exposed surfaces. As such, an insulative layer 27 covers almost the entire scissors 20. The only exposed surface portions of the scissors 20 that are not electrically and thermally insulated are two segments 28A and 28B on the confronting surfaces of the scissor jaws 22A and 22B adjacent their respective cutting edges. Therefore, although electrical energy is easily conducted through both jaws 22A and 22B, there is no flow of electrical energy into, nor out of, any exposed portion of the surgical scissors 20 other than into conductor 24 which enters the insulated surgical scissors 20 adjacent the handle portion (FIG. 1) and out of the segments 28A and 28B. Moreover, since the exit flow of electrical energy is confined to segments 28A and 28B of the scissors 20, the only portions of the scissors 20 that conduct heat are the segments 28A and 28B. As such, any burning or smoking of tissue caused by the surgical scissors 20 being electrically active is restricted to tissue trapped between the segments 28A and 28B. Therefore, with such a design, the insulated surgical scissors 20 prevents inadvertent injury to surrounding structures, such as, for example, to the common bile duct while dissecting the gall bladder out of the gall bladder bed.

Referring to FIG. 2A, the segments 28A and 28B completely overlap when the scissors 20 are in a closed condition. This ensures that no part of each segment 28A and 28B remains exposed to surrounding tissue when the jaws 22A/22B are completely closed. As such, when the surgeon energizes the segments 28A/28B only the tissue trapped between the segments 28A/28B are cauterized and any inadvertent burning of surrounding tissue is avoided.

Figure 8:
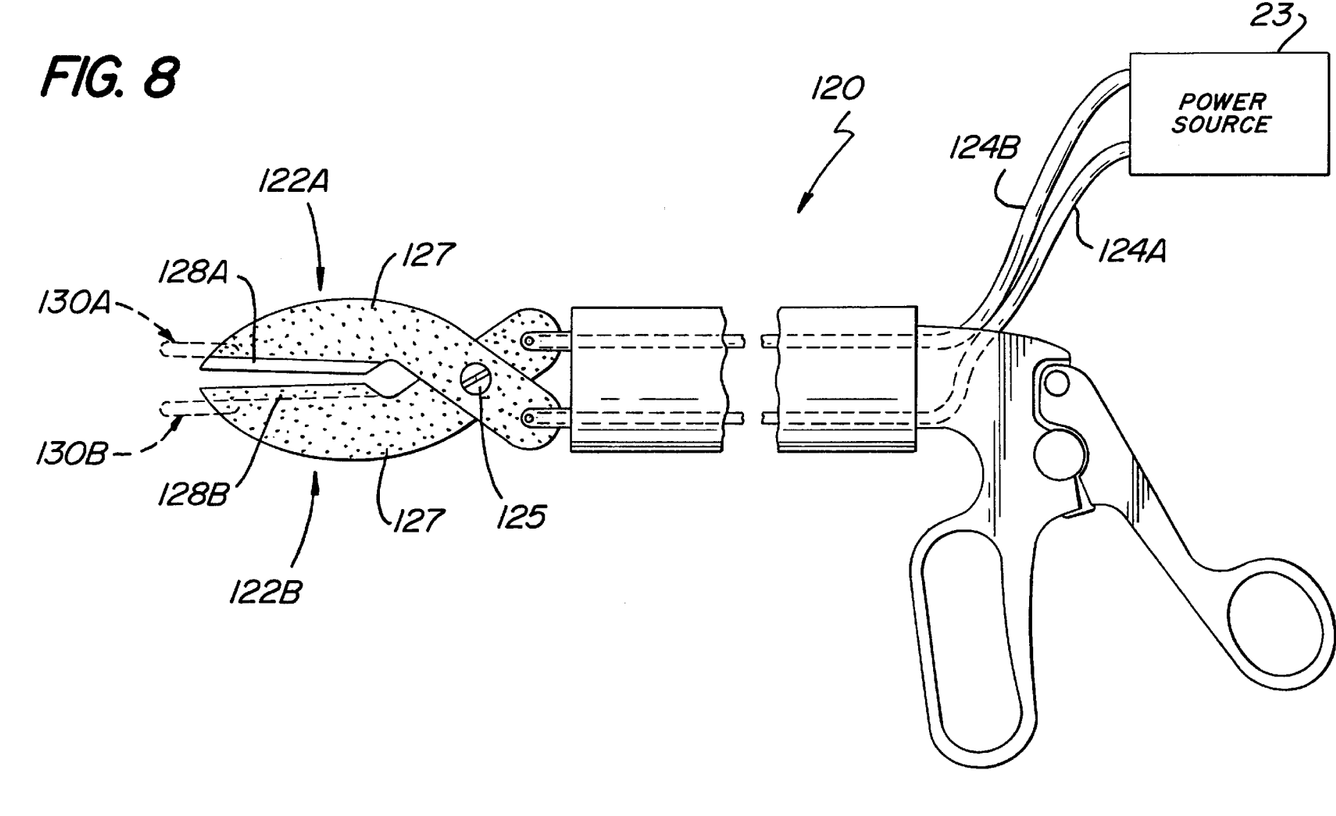
FIG. 8 is an enlarged fragmentary side elevational view of a bipolar embodiment of the insulated surgical scissors in accordance with this invention.

It is should be noted at this juncture that although an inclined segment 28A is depicted in FIG. 1, it is within the broadest aspect of this invention to include other segment 28A/28B configurations (e.g., a segment of a constant height as shown in FIG. 8 as indicated by the reference number 128A) that provide for electrically/thermally conductive segments that are completely covered when the jaws 22A/22B are in a closed condition (FIG. 2A). The important aspect of this invention is that no portion of the conductive segments 28A/28B is exposed to surrounding tissue when cauterization occurs.

Figure 3:
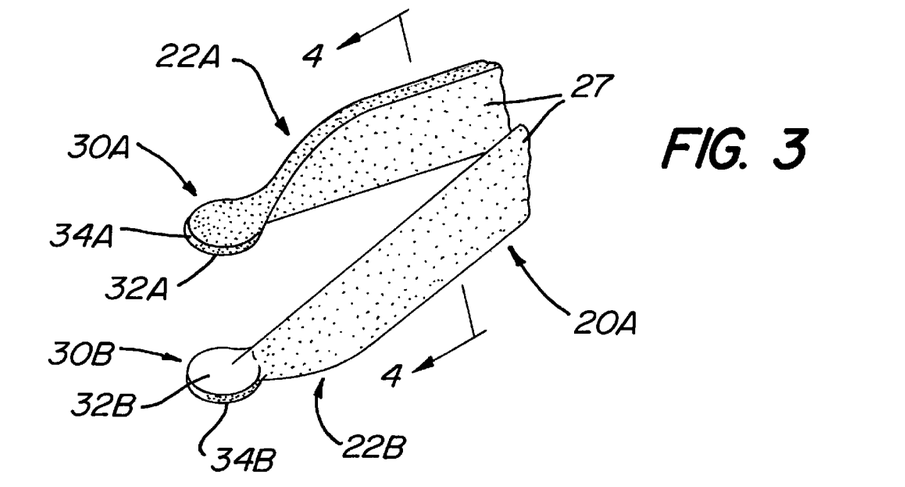
FIG. 3 is an enlarged isometric view of the working end of a second monopolar embodiment of the insulated surgical scissors in accordance with this invention.
Figures 4, 5, 6, 7:
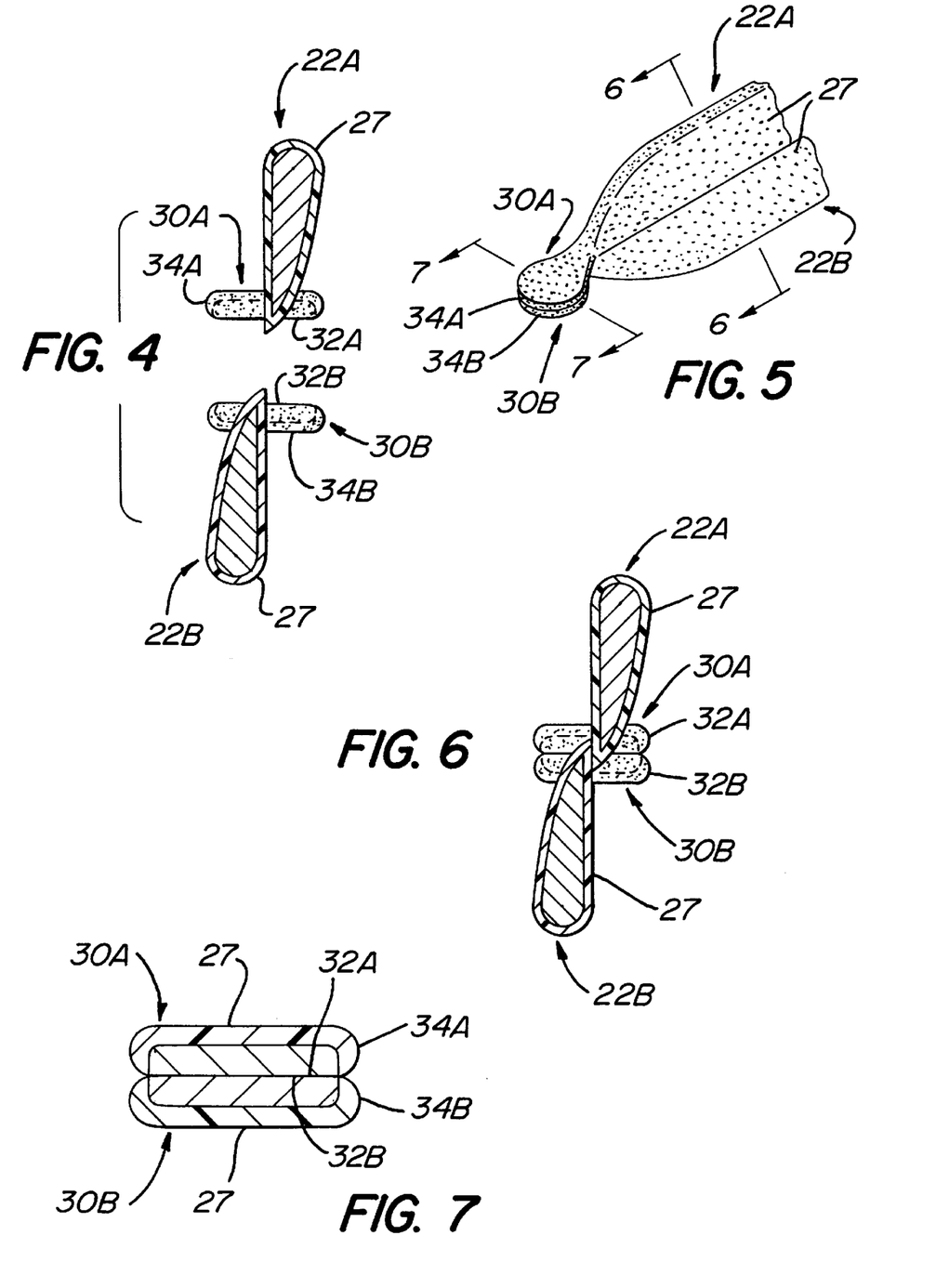
FIG. 4 is an enlarged view of the embodiment of FIG. 3 taken along line 4—4.
FIG. 5 is an enlarged view of the second monopolar embodiment of the insulated surgical scissors with the working end in a closed condition.
FIG. 6 is an enlarged view of the second monopolar embodiment of the insulated surgical scissors of taken along line 6—6 of FIG. 5.
FIG. 7 is a view of the second monopolar embodiment of the insulated surgical scissors taken along line 7—7 of FIG. 5.

Referring to FIG. 1 in a second monopolar embodiment of a surgical scissors, each jaw 22A and 22B includes electrically/thermally conductive flattened tips 30A and 30B, which are shown in phantom representation. These flattened tips 30A and 30B (as can be seen more clearly in FIG. 3) are generally round (approximately 2mm in diameter) and are used for seizing a vessel for cauterization. The tips 30A and 30B each comprise a metal similar to the metal of the respective jaws 22A and 22B and are contiguous with the respective jaw. In particular, these flattened tips 30A and 30B (hereinafter, "tips 30A and 30B") each comprise facing surfaces 32A and 32B that are electrically and thermally conductive. All other portions of the tips 30A and 30B, including the edges 34A and 34B are electrically and thermally insulated. These tips 30A and 30B can be used to compress and cauterize tissue trapped between the facing surfaces 32A and 32B. This is very useful in stopping large "bleeders", which are severed with the scissors 20. As shown in FIG. 1, the tips 30A and 30B are electrically and thermally conductive in conjunction with the segments 28A and 28B.

Referring to FIGS. 3–7, in another embodiment of this invention, an insulated surgical scissors 20A does not include electrically/thermally conductive segments, e.g., 28A and 28B. Rather, an insulative layer 27 covers each of the jaws 22A and 22B in their entirety as well as all surfaces of the electrically-conductive tips 30A and 30B except for the facing surfaces 32A and 32B thereof. During operation, the surgeon cuts with the blades of jaws 22A and 22B of the insulated surgical scissors 20A, and when he/she needs to coagulate a cut area, the surgeon initially opens the scissors 20A (FIG. 4), then closes the scissors 20A (FIGS. 5–7) to pinch the area to be cauterized between the facing, conductive surfaces 32A and 32B of the tips 30A and 30B. At that point the surgeon depresses a conventional power source foot pedal (not shown) to pass cauterizing current through the conductive surfaces for cauterizing the area that has been pinched between the tips.

The insulated surgical scissors 20 and 20A are particularly well suited for severing large tissue sections.

Figure 8A:
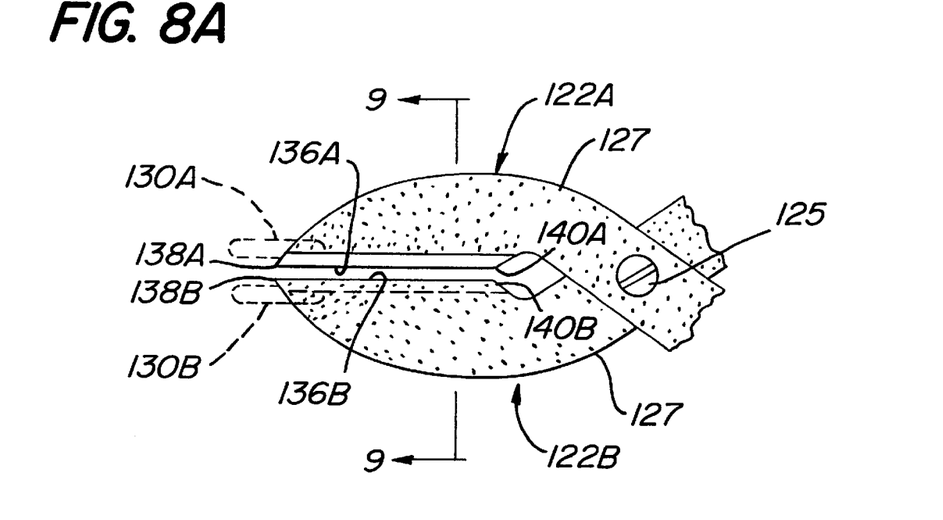
FIG. 8A is an enlarged view of the working end of the bipolar embodiment of the insulated surgical scissors.
Figures 9, 10:
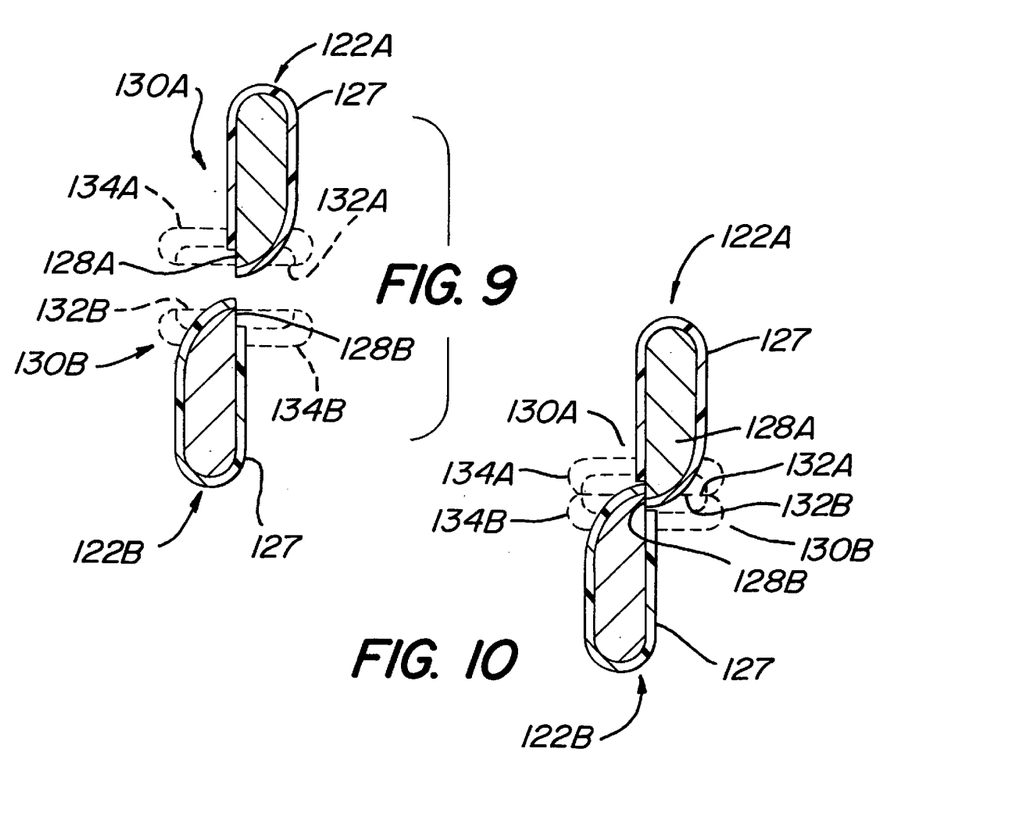
FIG. 9 is an enlarged cross-sectional view of a bipolar insulated surgical scissors having flattened tips taken along line 9—9 of FIG. 8A.
FIG. 10 is an enlarged cross-sectional view of the bipolar insulated surgical scissors having flattened tips taken along line 9—9 of FIG. 8A but showing the tips in a closed condition.

There is shown at 120 in FIGS. 8 and 8A an insulated surgical scissors having a pair of jaws 122A and 122B electrically coupled in a bipolar configuration. A bipolar configuration means that the each jaw forms an electrode with one jaw being at the voltage of the power source 23 while the other jaw is electrically coupled to the ground side of the power source 23. Hence, electrical energy flow is now confined to the following path: power source to one jaw (e.g., lower jaw 122B), through the tissue wedged between the pair of jaws, out into the other jaw (e.g., upper jaw 122A) and then back to the power source 23. As such, there is no conductive plate that the patient must lie on and there is no flow of current through the patient's body other than through the tissue between the jaws. In particular, an electrical conductor 124B brings electrical energy from the power source 23 to the lower jaw 122B, and another electrical conductor 124A provides the ground path from the upper jaw 122A to the ground side of the power source 23.

Actuation of the jaws 122A and 122B by the handle portion of the insulated surgical scissors 120 is similar to that described earlier with respect to the insulated surgical scissors 20.

Like the monopolar insulated surgical scissors 20, the bipolar insulated surgical scissors 120 is completely insulated (e.g., using a ceramic material), both electrically and thermally, on all of its exposed surfaces. As such, an insulative layer 127 covers almost the entire scissors 120. The only portions of the bipolar insulated surgical scissors 120 that are not electrically and thermally insulated are two electrically/thermally conductive segments 128A and 128B adjacent the respective cutting edges of the scissor jaws 122A and 122B. Therefore, although electrical energy is easily conducted through both jaws 122A and 122B, there is no flow of electrical energy into, nor out of, any exposed portion of the surgical scissors 120. It should be noted that the pivot point 125 between the upper and lower jaws 122A and 122B must be electrically and thermally insulated to ensure that there is no short that would cause the flow of electrical energy from the lower jaw 122B to the upper jaw 122A and thereby bypass the segments 128A and 128B. Moreover, since the exit flow of electrical energy is confined to segments 128A and 128B of the scissors 120, the only portions of the scissors 120 that conduct heat are the conductive segments 128A and 128B. As such, any burning or smoking of tissue caused by the surgical scissors 120 being electrically active is restricted to tissue trapped between the conductive segments 128A and 128B.

As is shown most clearly in FIG. 8A, the physical design of the upper jaw 122A and lower jaw 122B permits the conductive segments 128A and 128B to be brought together, whenever the surgical scissors 120 is closed by the surgeon, such that the contact along the entire length of their corresponding cutting edges 136A and 136B is simultaneous. In other words, the upper jaw 122A and lower jaw 122B are angled so that the front edge portions 138A/138B make contact at the same time that the rear edge portions 140A/140B make contact. Should the rear edge portions 140A/140B make contact before the front edge portions 138A/138B, an electrical short would occur causing electrical energy to flow across the rear edge portions 140A/140B and bypass flowing through any tissue trapped between the front edge portions 138A/138B.

It is should be noted at this juncture that it is within the broadest aspect of this invention to include other segment 128A/128B configurations that provide for electrically/thermally conductive segments that are completely covered when the jaws 122A/122B are in a closed condition. The important aspect of this invention is that no portion of the conductive segments 128A/128B is exposed to surrounding tissue when cauterization occurs.

It should also be noted that the conductive segments 128A/128B are employed to perform both the cutting and the coagulation functions. This is in contradistinction to U.S. Pat. No. 5,352,222 (Rydell) where the blade does the cutting and the blade support carries out the coagulation.

Referring to FIGS. 8 and 8A, in a second bipolar embodiment of a surgical scissors, each jaw 122A and 122B includes electrically/thermally conductive flattened tips 130A and 130B, which are shown in phantom representation. These flattened tips 130A and 130B are similar to the flattened tips 30A and 30B discussed previously. The tips 130A and 130B each comprise a metal similar to the metal of the respective jaws 122A and 122B and are contiguous with the respective jaw. In particular, these flattened tips 130A and 130B (hereinafter, "tips 130A and 130B") each comprise facing surfaces 132A and 132B that are electrically and thermally conductive. All other portions of the tips 130A and 130B, including the edges 134A and 134B are electrically and thermally insulated. These tips 130 and 130B can be used to compress and cauterize tissue trapped between the facing surfaces 132A and 132B. This is very useful in stopping large "bleeders", which are severed with the scissors 120. As shown in FIG. 8A, the tips 130A and 130B are electrically and thermally conductive in conjunction with the conductive segments 128A and 128B.

Figure 11:
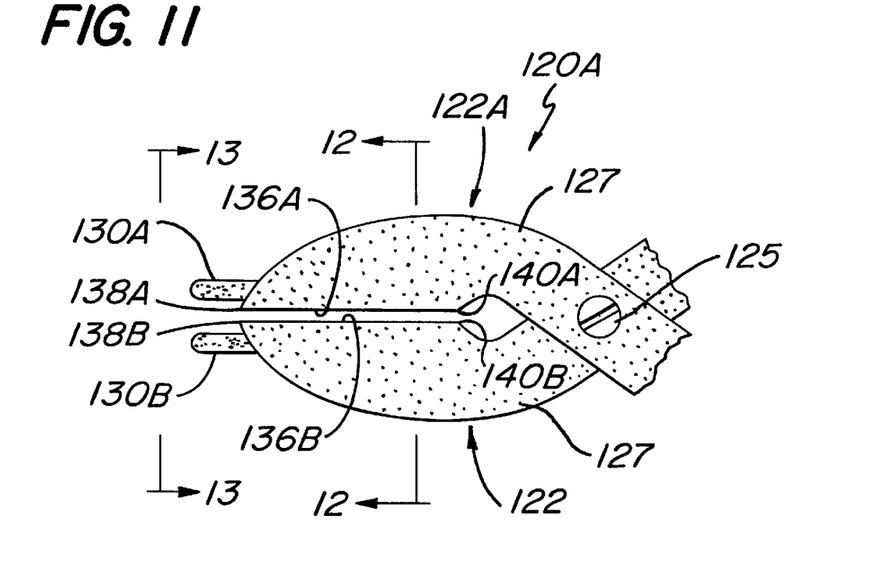
FIG. 11 is an enlarged side view of the working end of a second embodiment of a bipolar insulated surgical scissors in accordance with this invention.
Figures 12, 13:
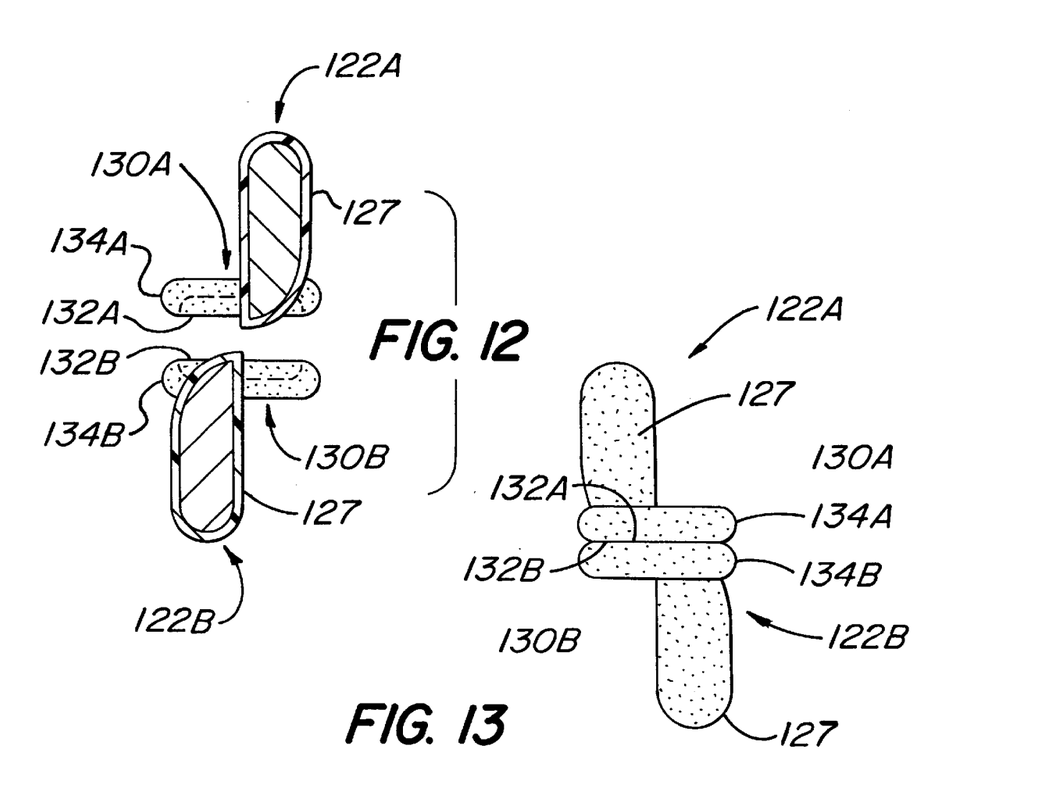
FIG. 12 is an enlarged cross-sectional view of the second embodiment of the bipolar insulated surgical scissors taken along line 12—12 of FIG.11.
FIG. 13 is an enlarged, front-end view cross-sectional view of the second embodiment of the bipolar insulated surgical scissors taken along line 13—13 of FIG. 11.

Referring to FIG. 11, in another embodiment of this invention, an insulated surgical scissors 120A does not include electrically/thermally conductive segments, e.g., 128A and 128B. Rather, an insulative layer 127 covers each of the jaws 122A and 122B in their entirety as well as all surfaces of the electrically-conductive tips 130A and 130B except for the facing surfaces 132A and 132B thereof. During operation, the surgeon cuts with the blades of jaws 122A and 122B of the insulated surgical scissors 120A, and when he/she needs to coagulate a cut area, the surgeon initially opens the scissors 120A (FIG. 11), then closes the scissors 120A (FIG. 13) to pinch the area to be cauterized between the facing, conductive surfaces 132A and 132B of the tips 130A and 130B. At that point the surgeon depresses a conventional power source foot pedal (not shown) to pass cauterizing current through the conductive surfaces 132A/132B for cauterizing the area that has been pinched between the tips 130A/130B.

Figure 14:
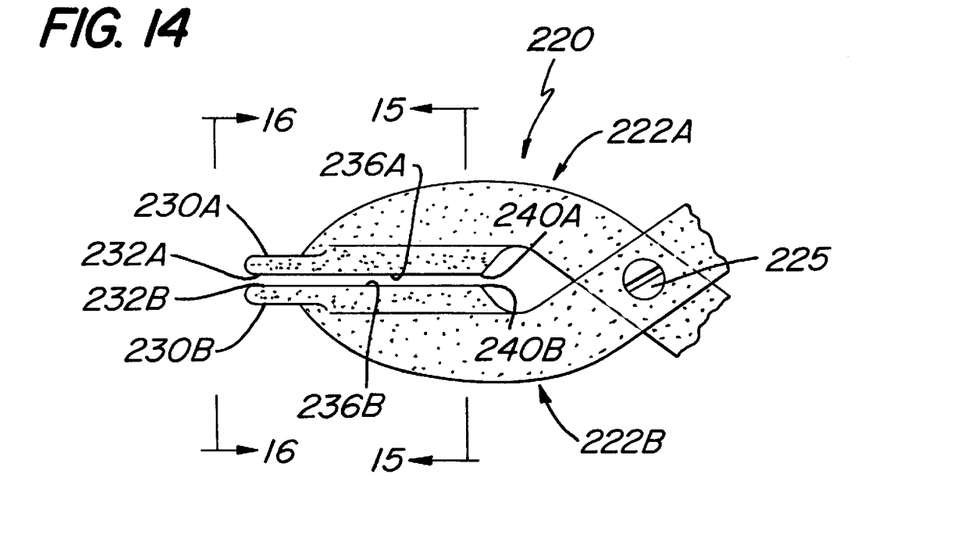
FIG. 14 is an enlarged side view of the working end of a third embodiment of a bipolar insulated surgical scissors in accordance with this invention.
Figure 15:
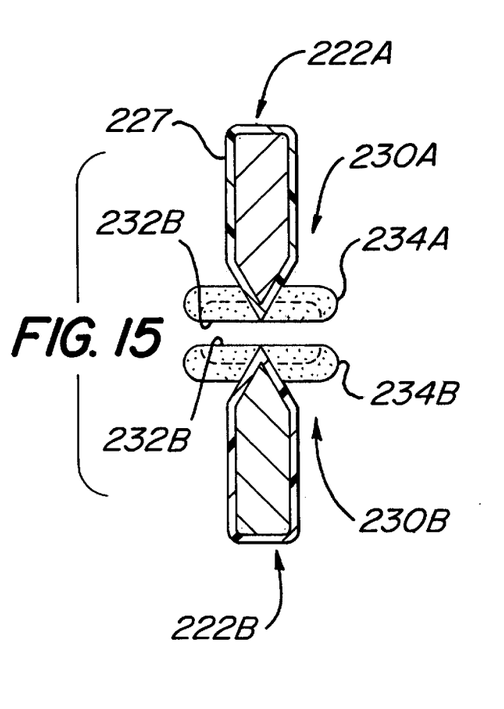
FIG. 15 is an enlarged cross-sectional view of the third bipolar insulated surgical scissors of FIG. 14 taken along line 15—15.
Figure 16:
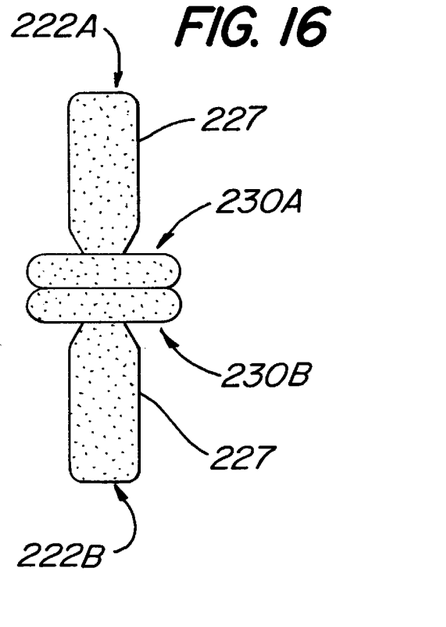
FIG. 16 is a cross-sectional view of the third bipolar insulated surgical scissors taken along line 16—16 of FIG. 14 but in a closed condition.

There is shown at 220 in FIG. 14 another bipolar insulated surgical scissors having a pair of jaws 222A and 222B that cut tissue by trapping the tissue between the blades of the jaws 222A/222B; however, the cutter jaws 222A/222B do not overlap and shear the tissue, as do the jaws of the insulated monopolar surgical scissors 20/20A and the insulated bipolar surgical scissors 120/120A. In particular, the bipolar insulated surgical scissors 220 has two distinctions from the insulated bipolar surgical scissors 120: (1) cutting edges 236A and 236B do not overlap (as do the cutting edges 136A and 136B) but rather abut in a manner similar to that of "nail clippers"; i.e., cutting occurs by "snipping" action wherein the edges 236A and 236B of the jaws 222A and 222B abut over their length simultaneously; (2) the insulated bipolar surgical scissors 220 includes flattened tips 230A and 230B that are disposed so that the facing surfaces 232A and 232B are coplanar with the respective cutting edges 236A and 236B so that they are able to grip and coagulate when the blades are closed, i.e., when the edges 236A and 236B have trapped tissue therebetween. In all other respects, the insulated bipolar surgical scissors 220 is identical to the embodiment of FIG. 11.

The jaws 222A and 222B are electrically coupled in a bipolar configuration. Hence, as discussed previously with the insulated bipolar surgical scissors 120/120A, electrical energy flow is confined to the following path: power source to one jaw (e.g., upper jaw 222A), through the tissue wedged between the pair of jaws, out into the other jaw (e.g., lower jaw 222B) and then back to the power source 23. As such, there is no conductive plate that the patient must lie on and there is no flow of current through the patient's body other than through the tissue between the jaws 222A/222B.

Like the insulated bipolar surgical scissors 120/120A, the bipolar insulated surgical scissors 220 is completely insulated (e.g., using a ceramic material), both electrically and thermally, on all of its exposed surfaces. As such, an insulative layer 227 covers almost the entire scissors 220. Each of the jaws 222A and 222B includes electrically conductive protruding tips 230A and 230B, respectively, as shown in FIG. 14. The tips 230A and 230B each comprise a metal similar to the metal of the respective jaws 222A and 222B and are contiguous with the respective jaw. These tips 230A and 230B can be used to compress tissue and to cauterize the tissue. Only the facing surfaces 232A and 232B are electrically and thermally conductive; the outer surfaces and edges 234A and 234B are electrically and thermally insulated. Therefore, although electrical energy is easily conducted through both jaws 222A and 222B, there is no flow of electrical energy into, nor out of, any exposed portion of the surgical scissors 220. It should be noted that the pivot fastener 225 between the upper and lower jaws 222A and 222B must be electrically and thermally insulated to ensure that there is no short that would cause the flow of electrical energy from the lower jaw 222B to the upper jaw 222A.

Moreover, since the exit flow of electrical energy is confined to tips 230A and 230B of the bipolar insulated surgical scissors 220, the only portions of the scissors 220 that conduct heat are the conducting surfaces 232A and 232B. As such, any burning or smoking of tissue caused by the surgical cutter 220 being electrically active is restricted to tissue trapped between the tips 230A and 230B.

The physical design of the upper jaw 222A and lower jaw 222B permits the jaws 222A and 222B to be brought together, whenever the surgical cutter 220 is closed by the surgeon, such that the contact along the entire length of their corresponding cutting edges 236A and 236B is simultaneous. In other words, the upper jaw 222A and lower jaw 222B are angled so that the facing surfaces 232A/232B contact at the same time that the cutting edge ends 240A/240B make contact. Should the edge ends 240A/240B make contact before the facing surfaces 232A/232B of the tips 230A/230B, an electrical short would occur causing electrical energy to flow across the edge ends 240A/240B and bypass flowing through any tissue trapped between the facing surfaces 232A/232B.

It should be understood that the construction of the working end (the cutting blades, cutting edges, flattened tips, monopolar and bipolar configurations, etc.) of each of the above-discussed embodiments can be employed in a non-laparoscopic construction (e.g., an open surgery construction).

Without further elaboration, the foregoing will so fully illustrate my invention that others may, by applying current or future knowledge, readily the same for use under various conditions of service.

I claim:

1. An apparatus for cutting and coagulating tissue during surgery while minimizing electrical and thermal contact of said apparatus with surrounding tissue, said apparatus comprising:

a pair of opposing electrically conductive cutting blades pivotally connected to allow for shearing action of any tissue confined between opposed cutting edges of said cutting blades, said blades having confronting surfaces, said pair of opposing cutting blades being entirely covered with an electrically and thermally insulative material except along corresponding segments of said confronting surfaces;

a power source coupled to at least one of said pair of opposing cutting blades for electrically and thermally energizing at least one of said pair of blades; and said apparatus including a closed condition wherein said confronting surfaces form overlapping surfaces, said overlapping surfaces including said corresponding segments.

2. The apparatus of claim 1 wherein each of said corresponding segments is adjacent a respective cutting edge.

3. The apparatus of claim 2 wherein said apparatus includes a closed condition wherein said confronting surfaces form overlapping surfaces, said overlapping surfaces defining said corresponding segments.

4. The apparatus of claim 1 wherein said cutting blades further comprise tips having facing surfaces, said facing surfaces being thermally and electrically conductive and cooperating to compress tissue disposed therebetween and to coagulate said tissue therebetween.

5. The apparatus of claim 1 wherein said pair of opposing cutting blades are constructed so that an entire length of one of said cutting edges simultaneously contacts an entire length of the other of said cutting edges when said cutting edges are brought toward one another with no tissue disposed therebetween.

6. The apparatus of claim 5 wherein each of said corresponding segments is adjacent a respective cutting edge.

7. The apparatus of claim 6 wherein said apparatus includes a closed condition wherein said confronting surfaces form overlapping surfaces, said overlapping surfaces defining said corresponding segments.

8. The apparatus of claim 5 wherein said cutting blades further comprise tips having facing surfaces, said facing surfaces being thermally and electrically conductive and cooperating to compress tissue disposed therebetween and to coagulate said tissue therebetween.

9. An apparatus for cutting and coagulating tissue during open surgery while minimizing electrical and thermal contact of said apparatus with surrounding tissue, said apparatus comprising:

a pair of opposing electrically conductive cutting blades pivotally connected to allow for cutting of any tissue confined between opposed cutting edge of said cutting blades, said pair of opposing cutting blades abutting each other during cutting, said pair of opposing cutting blades being entirely covered with an electrically and thermally insulative material, said cutting blades further comprising tips having facing surfaces, said facing surfaces being thermally and electrically conductive and cooperating to compress tissue disposed therebetween and to coagulate said tissue therebetween;

said pair of opposing cutting blades being constructed so that an entire length of one of said cutting edges simultaneously contacts an entire length of the other of said cutting edges when said cutting edges are brought toward one another with no tissue disposed therebetween; and a power source having a power side that is electrically coupled to one of said pair of opposing cutting blades and having a ground side that is electrically coupled to the other of said pair of opposing cutting blades for electrically and thermally energizing said one of said pair of blades.

10. An apparatus for cutting and coagulating tissue during surgery while minimizing electrical and thermal contact of said apparatus with surrounding tissue, said apparatus comprising:

a pair of opposing, electrically conductive cutting blades pivotally connected to cut any tissue confined between cutting edges of said cutting blades, said pair of opposing cutting blades being entirely covered with an electrically and thermally insulative material except on minor tissue-contacting portions of confronting surfaces of said cutting blades; and a power source coupled to at least one of said pair of opposing cutting blades for electrically and thermally energizing at least one of said pair of blades.

11. The apparatus of claim 10 wherein said minor tissue-contacting portions are facing surfaces of cutting blade tips, said facing surfaces being thermally and electrically conductive and cooperating to compress tissue disposed therebetween and to coagulate said tissue therebetween.

12. The apparatus of claim 11 wherein said cutting blades are constructed to nip any tissue confined between said cutting edges, and so that an entire length of one of said cutting edges simultaneously contacts an entire length of the other of said cutting edges when said cutting edges are brought toward one another with no tissue disposed therebetween.

13. The apparatus of claim 11 wherein the cutting edges of said cutting blades abut each other during cutting.

14. The apparatus of claim 11 wherein said pair of opposing cutting blades are pivotally connected to allow for shearing action of any tissue confined between the cutting edges thereof.

* * * * *